United States Patent [19]

Jandacek

[11] 4,264,583

[45] Apr. 28, 1981

[54] GALLSTONE DISSOLUTION COMPOSITIONS AND METHOD

[75] Inventor: Ronald J. Jandacek, Cincinnati, Ohio

[73] Assignee: The Procter & Gamble Company, Cincinnati, Ohio

[21] Appl. No.: 60,538

[22] Filed: Jul. 25, 1979

[51] Int. Cl.$^3$ .............................................. A61K 31/56
[52] U.S. Cl. .................................... 424/240; 260/397.1
[58] Field of Search ............................. 424/180, 240; 260/397.1

[56] References Cited

U.S. PATENT DOCUMENTS

| | | | |
|---|---|---|---|
| 3,600,186 | 8/1971 | Mattson et al. | 99/1 |
| 3,859,437 | 1/1975 | Weigand | 424/238 |
| 3,954,976 | 5/1976 | Mattson et al. | 424/180 |
| 3,963,699 | 6/1976 | Rizzi et al. | 260/234 R |
| 4,005,195 | 1/1977 | Jandacek | 424/180 |
| 4,005,196 | 1/1977 | Jandacek et al. | 4524/180 |
| 4,034,083 | 7/1977 | Mattson | 424/180 |
| 4,079,133 | 3/1978 | Drees et al. | 424/238 |
| 4,105,794 | 8/1978 | Drell et al. | 424/317 |
| 4,158,707 | 6/1979 | Steffen | 424/244 |

OTHER PUBLICATIONS

"Metabolism", 28 (10), 994–1000 (1979).
British Med. J. (1978), article by Maudgal et al., pp. 851–853.
Thistle et al., "New England J. Med.", Sep. 27, 1973, pp. 655–659.
Summerfield et al., "Gastroenterology" (1975), vol. 69, pp. 998–1000.
Thistle et al., "Gastroenterology", vol. 61 (1971), No. 4, pp. 488–496.
New England Journal of Med. (1977), vol. 296, No. 21, pp. 1185–1190.
The Lancet, May 10, 1975, p. 1083.
Redinger et al., Clin. Res., vol. 66 (1976), p. 666A.
Wood et al., "Metabolism" (1972), vol. 21, p. 107.
J. Lab. Clin. Med. (1977), vol. 89, p. 354, Grundy et al.
Garcia-Romero et al., J. Sur. Research (1978), No. 24, pp. 62–64.
Makino et al., "J. Lipid Research (1978)", No. 19, pp. 723–728.

*Primary Examiner*—Elbert L. Roberts
*Attorney, Agent, or Firm*—Michael J. Roth; Steven J. Goldstein; Richard C. Witte

[57] ABSTRACT

Polyol fatty acid polyesters are safe and effective agents for dissolving radiolucent gallstones when administered orally, either alone or, preferably, in conjunction with a litholytic bile acid.

19 Claims, No Drawings

GALLSTONE DISSOLUTION COMPOSITIONS AND METHOD

TECHNICAL FIELD

At least 15 million Americans are estimated to have gallstones, most of which are composed chiefly of cholesterol. Cholesterol is solubilized in bile by mixed micelles of bile acids and lecithin, and bile that is supersaturated with cholesterol is predisposed to gallstone formation and growth due to crystallization of excess cholesterol from solution. Indeed, after overnight fasting, most patients who have cholesterol (radiolucent) gallstones have bile saturated or supersaturated with cholesterol. Although the factors responsible for the crystallization of cholesterol from supersaturated bile are poorly understood, studies in the past have indicated that unsaturated bile or similar unsaturated micellar solutions are capable of dissolving cholesterol gallstones.

Symptomatic cholelithiasis is a surgically treated disease. Medical (non-surgical) management of symptomatic gallstones in the past has been unsatisfactory, because low fat diets and anti-cholinergic drugs have been unable to prevent recurrent attacks of biliary colic.

More recently, it has been discovered that prolonged treatment with chenodeoxycholic acid (CDCA), a litholytic bile acid, gradually dissolves radiolucent gallstones in 50 to 60 percent of treated patients.

Chenodeoxycholic acid treatment makes bile unsaturated in cholesterol, thus dissolving radiolucent stones. The mechanism of action of chenodeoxycholic acid is in dispute, and there has been some concern that lithocholic acid, generated from chenodeoxycholic acid, may cause hepatotoxicity. A significant number of patients treated with chenodeoxycholic acid show increases in serum glutamic oxaloacetic transaminase (SGOT) activity.

Ursodeoxycholic acid (UDCA), first isolated from the bile of bears, also dissolves radiolucent gallstones, but does so at lower doses, and without diarrhea or alterations in hepatic function.

It has also been shown that a reduction in dietary cholesterol concomitant with litholytic bile acid therapy enhances the effect of the litholytic bile acid by further increasing the bile acid/cholesterol ratio in bile. Unfortunately, current pharmaceutical products which effect a reduction in serum cholesterol have a tendency to cause, rather than dissolve, gallstones. Even cholesterol-lowering diets can predispose to an increased incidence of gallstones. See R. A. L. Sturdevant, et al., *N. Engl. J. Med.* 288:24 (1973).

It has now been discovered that polyol fatty acid polyesters, by preventing cholesterol resorption in the gut, safely and effectively reduce both serum and bile cholesterol levels, which results in gallstone dissolution and enhances the effects of litholytic bile acids. Polyol fatty acid polyesters are also taught to inhibit intestinal absorption of lipophilic materials such as cholesterol, fat-soluble vitamins, and lipophilic toxins. Yet it has also now been discovered that polyol fatty acid polyesters do not interfere appreciably with the absorption of litholytic bile acids, which are virtually water insoluble. By contrast, cholesterol reduction agents which act by binding bile acids are clearly unacceptable for concurrent or combined administration with litholytic bile acids.

The present invention provides a method of treatment and prevention of gallstones comprising the administration of the non-lithogenic cholesterol reduction agents, polyol fatty acid polyesters, either alone or together with litholytic bile acids, such as CDCA and UDCA. The present invention also provides novel compositions which conveniently contain both polyol fatty acid polyesters and a litholytic bile acid. Such methods and compositions are safe and effective even in persons without elevated cholesteral levels, but who are suffering from gallstones.

BACKGROUND ART

Treatment of endogenous disease states, such as hypercholesterolemia, with the polyesters employed in the present invention is known to the art. Relevant patents include: U.S. Pat. No. 3,600,186 issued Aug. 17, 1971 to Mattson, et al., which discloses and claims a low calorie, fat-containing food composition where from about 10% to about 100% of the total fat consists of polyol fatty acid polyesters.

U.S. Pat. No. 3,954,976 issued May 4, 1976 to Mattson, et al., encompasses polyol fatty acid polyesters in 0.1–5 gram unit doses as pharmaceutical compositions for inhibiting the absorption of cholesterol.

U.S. Pat. No. 3,963,699 issued June 15, 1976 to Rizzi, et al., relates to a solvent-free esterification process for preparing the polyol fatty acid polyesters. A sugar, a fatty acid $C_1$–$C_2$ alkyl ester, an alkali metal fatty acid soap and a base catalyst (alkali metal alloys, alkali metal hydrides, alkali metal alkoxides) are heated to form a homogeneous melt; excess fatty acid alkyl ester is added to form the polyol fatty acid polyesters, which are then separated from the mixture. The process allows drug-quality polyol fatty acid polyesters to be manufactured without a solvent-removal step.

U.S. Pat. No. 4,005,195 issued Jan. 25, 1977 to Jandacek describes anti-anal leakage (AAL) agents used in combination with the liquid polyol fatty acid polyesters. The disclosure relates to: (1) compositions of matter comprising polyol fatty acid polyesters+anti-anal leakage compounds; (2) low calorie foods with polyol fatty acid polyesters+AAL compounds: (3) polyol fatty acid polyesters+AAL in unit dose form as pharmaceuticals; and (4) methods for treating hypercholesterolemia by inhibiting absorption of cholesterol without anal leakage by administering compositions per (1).

U.S. Pat. No. 4,005,196 issued Jan. 25, 1977 to Jandacek, et al., encompasses compositions comprising fat-soluble vitamins in combination with polyol fatty acid polyesters and anti-anal leakage agents.

U.S. Pat. No. 4,034,083 issued July 5, 1977 to Mattson discloses polyol fatty acid polyesters plus fat-soluble vitamins.

Treatment of gallstones by administration of chenodeoxycholic acid is taught by L. S. Goodman and A. Gilman, eds. *The Pharmacological Basis of Therapeutics*, 5th ed. (1975) p. 972 and references there cited.

J. L. Thistle and L. J. Schoenfield, *Gastroenterology* 61:488 (1971) teach that clofibrate, used in the treatment of hypercholesterolemia, causes bile to become supersaturated with cholesterol.

The Coronary Drug Project Research Group, *N. Engl. J. Med.* 296:1186 (May 26, 1977) and J. A. Heady, *Bull. WHO* 48:243 (1973) describe two large clinical trials of clofibrate, and report a significantly increased incidence of gallbladder disease in patients taking clofibrate.

R. N. Redinger and D. M. Grace, *Clin. Res.* 66:666A (1976) report increased saturation of bile with cholesterol and formation of cholesterol gallstones in monkeys experimentally administered cholestyramine, another drug prescribed in the treatment of hypercholesterolemia.

Cholestyramine is also taught to reduce biliary levels of chenodeoxycholic acid. See P. D. Wood, et al., *Metabolism* 21:107 (1972).

An incident involving increased biliary cholesterol levels and development of gallstones in a patient receiving colestipol, also used to treat high serum cholesterol levels, has been reported by S. M. Grundy and H. Y. I. Mok, *J. Lab. Clin. Med.* 80:354 (1977).

E. Garcia-Romero, et al., *J. Surg. Res.* 24:62 (1978) disclose the in vitro dissolution of a cholesterol gallstone by immersing the gallstone in a solution of 1500 mg. clofibrate in 5 ml. ethanol—clearly unacceptable as a medical treatment.

L. R. Krasno and D. C. Harrison, *N. Engl. J. Med.* 297:669 (1977) suggest that elevations of cholesterol concentration in the bile caused by clofibrate may be due to an underlying basic defect in cholesterol metabolism.

I. Makino, et al., *J. Lipid Res.* 19:723 (1978) describes changes in biliary lipid and biliary bile acid composition in patients after administration of ursodeoxycholic acid.

*New Scientist*, 82:27 (1979) summarizes the status of current research on ursodeoxycholic acid.

The disclosures of the foregoing patents and publications are hereby incorporated herein by reference.

DISCLOSURE OF THE INVENTION

The present invention provides oral compositions for prevention and treatment of radiolucent gallstones, comprising a safe and effective amount of a non-absorbable, non-digestible polyol fatty acid polyester of the type disclosed hereinafter, and a safe and effective amount of a litholytic bile acid, or pharmaceutically-acceptable salt thereof.

The polyol fatty acid polyesters used in the present compositions are those disclosed by Mattson, et al., in the above-cited references, which preferably contain at least four fatty acid groups and no more than about two free hydroxyl groups. As disclosed by Mattson, et al., preferred fatty acid ester groups in the polyol fatty acid polyester contain from about 14 to about 18 carbon atoms. Preferred polyols include erythritol, xylitol, sorbitol, glucose and sucrose, with sucrose being most preferred. Especially preferred sucrose fatty acid polyesters are the hexaoleate, heptaoleate and octaoleate of sucrose, and mixtures thereof.

When it is desired to administer compositions containing more than about 10 grams liquid polyol fatty acid polyester per day, undesired leakage of the liquid polyester through the anal sphincter can be avoided by the use of a composition comprising said non-absorbable, non-digestible liquid polyol fatty acid polyester, a safe and effective amount of a litholytic bile acid, and sufficient anti-anal leakage agent of the type disclosed by Jandacek (above) to prevent leakage of the liquid polyester through the anal sphincter.

The polyol fatty acid polyesters can interfere with absorption of fat-soluble vitamins, and this undesirable effect can be dealt with by co-administration of fat-soluble vitamins as taught by Mattson (above). Accordingly, alternative compositions for prevention and treatment of radiolucent gallstones comprise a safe and effective amount of the non-absorbable, non-digestible liquid polyol fatty acid polyester, a safe and effective amount of a litholytic bile acid, and sufficient fat-soluble vitamins selected from the group consisting of vitamin A, vitamin D, vitamin E and vitamin K, and mixtures thereof, to prevent abnormally low levels of said fat-soluble vitamins in humans or animals ingesting said composition. The anti-anal leakage agent can also be present in such compositions.

The present invention also provides a method for prevention and treatment of radiolucent gallstones, comprising administering to a human or lower animal in need of such treatment a therapeutically-effective amount of a composition comprising a non-absorbable, non-digestible polyol fatty acid polyester. Since the polyol fatty acid polyesters enhance the litholytic activity of litholytic bile acids, a preferred method for prevention and treatment of radiolucent gallstones comprises administering a polyol fatty acid polyester, as herein described, either in combination in the same dosage form with a litholytic bile acid, or concurrently with a litholytic bile acid in a separate dosage form.

Preferred litholytic bile acids used herein are those selected from the group consisting of chenodeoxycholic acid, ursodeoxycholic acid, and their pharmaceutically-acceptable salts, and mixtures thereof.

POLYOL POLYESTERS

The polyol polyesters (or, simply, "polyesters") employed in this invention comprise well-defined polyol fatty acid esters. The polyol starting material must have at least four esterifiable hydroxyl groups. Examples of suitable polyols are sugars, especially monosaccharides and disaccharides, and sugar alcohols. Examples of monosaccharides containing four hydroxyl groups are xylose and arabinose and the sugar alcohol derived from xylose, i.e., xylitol. The monosaccharide erythrose starting material is not suitable for the practice of this invention since it only contains three hydroxyl groups but the sugar alcohol derived from erythrose, i.e., erythritol, contains four hydroxyl groups and accordingly can be used. Suitable five hydroxyl group-containing monosaccharides are galactose, fructose and sorbose. Sugar alcohols containing six hydroxyl groups derived from sucrose, glucose and sorbose, e.g., sorbitol, are also suitable. Examples of disaccharide polyols which can be used include maltose, lactose and sucrose, all of which contain eight hydroxyl groups.

Preferred polyols for preparing the esters for use in the present invention are selected from the group consisting of erythritol, xylitol, sorbitol, glucose and sucrose. Sucrose is especially preferred.

The polyol starting material having at least four hydroxyl groups must be esterified with a fatty acid having from about 8 to about 22 (preferably 14-18) carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic and erucic acid. The fatty acids can be derived from naturally occurring or synthetic fatty acids; they can be saturated or unsaturated, including positional and geometrical isomers, depending on the desired physical properties, for example liquid or solid, of the polyol fatty acid ester compound.

The following are examples of suitable polyol fatty acid esters containing at least four fatty acid ester groups suitable for use in the present invention: glucose tetraoleate; glucose tetrastearate; glucose tetraester of mixed soybean oil fatty acids; mannose tetraester of tallow fatty acids; galactose tetraester of olive oil fatty acid; arabinose tetraester of cottonseed oil fatty acid; xylose tetralinoleate; galactose pentastearate; sucrose hexaoleate; sucrose octaoleate; sucrose octaester of substantially completely hydrogenated soybean oil fatty acid; sucrose octaester of peanut oil fatty acid. As noted before, highly preferred polyol fatty acid esters are those wherein the fatty acids contain from about 14 to about 18 carbon atoms and are thus derived from such natural materials as soybean oil, tallow, palm oil and olive oil. Examples of such compounds are the erythritol tetraester of olive oil fatty acid, erythritol tetraoleate, xylitol pentaoleate, sorbitol hexaoleate, sucrose octaoleate and sucrose octaester of soybean oil fatty acid.

A complete description of the fatty acid polyol polyesters used herein is found in U.S. Pat. Nos. 3,954,376 and 3,600,186, cited above.

A method of preparing polyol fatty acid polyesters which is especially preferred for the food and pharmaceutical compositions employed herein because it is solvent-free, does not generate difficult-to-remove contaminants and produces high yields is described in U.S. Pat. No. 3,963,699, cited above.

LITHOLYTIC BILE ACIDS

Chenodeoxycholic acid (CDCA) is a naturally-occurring bile acid. It is the predominant constituent of the bile of domestic fowl such as chickens. It also occurs in lesser amounts in the bile of other common domestic animals, and one source for this material is its isolation from naturally-occurring sources. However, the isolation or synthesis of CDCA by itself constitutes no part of the present invention.

CDCA can be prepared synthetically by a number of routes. Its preparation from cholic acid is described by Fieser, et al., *J. Am. Chem. Soc.* 72:5530 (1950) and Hauser, et al., *Helv. Chim. Acta* 43:1595 (1960). Its preparation by desulfuration of the 12-thioketyl derivative of methyl cholate 3,7-diacetate is described by Sato and Ikekawa, *J. Org. Chem.* 24:1367 (1959). The disclosures of the foregoing references are hereby incorporated herein by reference.

Ursodeoxycholic acid is the 7β epimer of chenodeoxycholic acid. It is found, in combination with taurine, in the bile of bears, and one source for UDCA is isolation from naturally occurring sources. This isolation is described by Shoda, *J. Biochem.* (Japan) 7:505 (1927). It is also available in high purity by commercial synthesis from companies such as Tokyo Tanabe Pharmaceutical Co. (Tokyo, Japan). However, the isolation or synthesis of UDCA by itself constitutes no part of the present invention.

The litholytic bile acids are virtually insoluble in water, but their emulsifying properties render them amenable to combination in dosage forms containing both water and oleaginous materials, such as polyol fatty acid polyesters. Both materials are freely soluble in ethanol. CDCA is tasteless in the acid form and thus can be used in a variety of palatable dosage forms with polyol fatty acid polyesters, such as margarines, food emulsions, etc. The sodium salt of CDCA is slightly sweet with a bitter aftertaste, and UDCA forms bitter crystals, so these are preferably used in dosage forms such as pills and capsules.

By "litholytic bile acid" herein is also meant the naturally occurring conjugates of chenodeoxycholic acid and ursodeoxycholic acid with the amino acids taurine and glycine, i.e., taurochenodeoxycholic acid, glycochenodeoxycholic acid, tauro-ursodeoxycholic acid, and glycoursodeoxycholic acid.

VITAMINS

The physicochemical properties of the polyol polyesters of the present invention cause them to undesirably interfere with uptake of fat-soluble vitamins. This type of interference with the absorption of vitamins A and E has been demonstrated in human volunteers who consumed polyol fatty acid polyesters. The consequence of polyol fatty acid polyester ingestion was a drop in the blood (plasma) levels of these vitamins.

To prevent the vitamin depletion problem, the polyol polyesters used herein can be fortified with fat-soluble vitamins, especially vitamin A, vitamin E and vitamin D, and mixtures thereof. (The polyesters can also be fortified with vitamin K. However, since the body can synthesize vitamin K, supplementation of the polyesters therewith is probably not critical to adequate nutrition in the normal subject.)

By "treatment" of radiolucent gallstones herein is meant dissolving or otherwise reducing the size of said gallstones.

By "safe and effective amount" or "therapeutically effective amount" of the polyol polyesters and litholytic bile acids herein is meant an amount which is effective to prevent, to dissolve, or to reduce the size of radiolucent gallstones and yet causes minimal or no undesirable side effects (at a reasonable benefit risk ratio) when the compositions are administered to humans or animals.

BEST MODE

As can be seen from the foregoing, the present invention provides compositions and methods for treatment of gallstones in humans and lower animals, comprising orally administering to a human or lower animal afflicted with gallstones a therapeutically-effective amount of a composition comprising a non-absorbable, non-digestible polyol fatty acid polyester and, preferably, at least one litholytic bile acid. Preferred polyol fatty acid polyesters used herein are the hexa-, hepta- and octa-oleates of sucrose (especially sucrose octaoleate) and mixtures thereof.

Preferred litholytic bile acids are CDCA and UDCA.

In general, the preferred compositions are orally administered at a rate from about 0.3 mg. per kilogram of body weight per day to about 3 g. per kilogram of body weight per day.

This invention also encompasses a method for treatment of cholelithiasis in humans and lower animals in need of such treatment with minimal anal leakage effect, comprising orally administering to a human or lower animal afflicted with gallstones a therapeutically-effective amount of a composition comprising from about 50% to about 90% by weight of a non-absorbable, non-digestible liquid polyol fatty acid polyester having at least 4 fatty acid ester groups, and from about 10% to about 50% by weight of an anti-anal leakage agent, preferably with a safe and effective amount of at least one litholytic bile acid.

The invention also encompasses a method for treating humans and lower animals afflicted with gallstones without decreasing the body's stores of fat-soluble vitamins comprising orally administering to a human or lower animal in need of such treatment a therapeutically-effective amount of a composition comprising a major portion of a non-absorbable, non-digestible polyol fatty acid polyester (especially the liquid polyesters) having at least 4 fatty acid ester groups, and sufficient fat-soluble vitamin selected from the group consisting of vitamin A, vitamin D, vitamin E and vitamin K, and mixtures thereof, to prevent abnormally low levels of said fat-soluble vitamins in humans or lower animals ingesting said composition and a safe and effective amount of chenodeoxycholic acid.

When a patient is on a long-term treatment regimen, both the anal leakage problem and the vitamin depletion problem are prevented by using highly preferred compositions of the following type:

a. from about 50% to about 90% of a non-absorbable, non-digestible liquid polyol fatty acid polyester selected from the group consisting of the hexaoleate, heptaoleate, and octaoleate of sucrose, and mixtures thereof;

b. from about 10% to about 50% by weight of an anti-anal leakage agent comprising hydrogenated palm oil;

c. sufficient fat-soluble vitamin selected from the group consisting of vitamin A, vitamin D, vitamin E and vitamin K, and mixtures thereof, to prevent abnormally low levels of said fat-soluble vitamins in animals ingesting said composition; and d. from about 1% to about 10% by weight of a litholytic bile acid selected from CDDA, UDCA, and pharmaceutically-acceptable salts thereof.

METHODS OF ADMINISTRATION

The dosages described herein are intended to administered orally, including any suitable unit dosage form such as pills, tablets and capsules. A preferred unit dosage form is capsules made from gelatin. The polyol ester and bile acid can also be administered "neat."

The pharmaceutical compositions employed herein can comprise the litholytic bile acid-sucrose polyester agent alone, in combination with vitamins, anti-anal leakage agents, or both, either directly or in combination with any desired, non-interfering pharmaceutical carrier. As used herein, the term "pharmaceutical carrier" means a solid or liquid filler, diluent or encapsulating substance. Some examples of the substances which can serve as pharmaceutical carriers are sugars such as lactose, glucose and sucrose; starches such as corn starch and potato starch; cellulose and its derivatives such as sodium carboxymethylcellulose, ethylcellulose and cellulose acetate; powdered tragacanth; malt; gelatin; talc; oils such as peanut oil, cottonseed oil, sesame oil, olive oil, corn oil and soybean oil; polyols such as propylene glycol, glycerin, sorbitol, mannitol and polyethylene glycol; agar; alginic acid; pyrogen-free water; isotonic saline; ethyl alcohol and phosphate buffer solutions, as well as other non-toxic compatible substances used in pharmaceutical formulations. Wetting agents and lubricants such as sodium lauryl sulfate, as well as coloring agents, flavoring agents and preservatives can also be present in the compositions, according to the desires of the formulator.

The pharmaceutical carriers of the foregoing type can optionally be employed in conjunction with the polyesters herein to provide practical size-to-dosage relationship composition forms which can be easily ingested, and means for providing accurate unit dosages in a convenient form. The pharmaceutical carrier usually will comprise from about 5% to about 50% by weight of the total pharmaceutical composition.

TYPICAL FORMULATIONS

The total AAL agent employed in any of the compositions herein will depend somewhat on the total amount of liquid polyester component of the compositions herein being ingested per day. The anti-anal leakage agent should be present in an amount equaling at least about 10% by weight of the liquid polyester. It is more preferred that the AAL agent comprises at least about 20% by weight of the liquid polyester to ensure that anal leakage does not occur, even at high ingestion rates. Compositions wherein the weight of AAL agent comprises from about 20% to about 50% of the weight of liquid polyester in conjunction with chenodeoxycholic acid provide excellent gallstone dissolution without anal leakage of the liquid polyol polyester.

Compositions comprising edible fatty acids, their edible salts or their edible, digestible esters as the AAL agent preferably comprise from about 10% to about 50% of these materials by weight of polyester. Compositions using palatable position-specific triglycerides as the AAL agent preferably comprise about 20% to about 40% (by weight of liquid polyester) of these AAL agents. When the edible, non-digestible solid polyesters are used as the AAL agent, they are preferably used at a rate of from about 20% to about 50% by weight of the liquid polyester.

The amount of the individual fat-soluble vitamins used to fortify the present compositions will vary with the age of the recipient, the dosage regimen used, and the amount of the vitamin ingested from other dietary sources. For example, in younger, growing children or in pregnant females it is recognized that larger amounts of any given vitamin should be ingested to supply optimal nutritional benefits than are needed with adult males. If the user of the present compositions happens to ingest foods which are extremely rich in a given fat-soluble vitamin, less of that vitamin need be used in the present compositions to ensure adequate intestinal uptake for good nutrition. In any event, an attending physician can, if so desired, measure the body levels of fat-soluble vitamins. Based on these data, the appropriate type and amount of fat-soluble vitamin used to fortify the polyesters herein can then be determined on an individual basis.

More simply, the formulator of the compositions herein can fortify the polyesters with a recommended daily allowance (RDA), or increment or multiple of an RDA, of any of the fat-soluble vitamins to ensure that the user of the compositions will maintain a nutritionally adequate uptake of said vitamins. For example, with vitamin A a daily amount in the range of 20 international units (I.U.) to about 57 I.U. per kilogram of body weight can be employed. With vitamin D, fortification of the compositions to provide about 400 I.U., total, per day is ample. When supplementing with vitamin E, the amount of the vitamin optimal for dietary intake ranges from 3-6 I.U. for infants to 25-30 I.U., total, per day for adults. When supplementing with vitamin K, it is more difficult to estimate the amount to be ingested to provide adequate nutrition since the microorganisms living in the intestine can synthesize this vitamin. However, it is known that ingestion of from 0.5 mg. to 1 mg. of vitamin K per day will prevent insufficiency.

As can be seen from the foregoing, the amount of the fat-soluble vitamins employed herein to fortify the polyesters can vary. In general in the preferred practice of the present invention, the polyesters are fortified with sufficient fat-soluble vitamin to provide from about 0.08% to about 150% of the average RDA.

DOSAGE

When the polyol fatty acid polyesters of the present invention are used alone for the dissolution of radiolucent gallstones, it is desirable to administer as large a dose as is reasonably possible while minimizing anal leakage. In adults, this dose will generally range from about 0.3 to about 1 mg. per kg., depending on the individual. Patients can be started on a treatment regimen at the lower end of this dosage range, and the dosage can be gradually increased until anal leakage occurs, and then decreased slightly.

When the polyol fatty acid polyesters are administered either in combination with or concurrently with chenodeoxycholic acid, the initial dose of CDCA is 750 mg. a day. The dosage of CDCA is adjusted upward until diarrhea due to the CDCA occurs and then diminished by 250 mg. for maintenance.

Unlike CDCA, the litholytic activity of ursodeoxycholic acid does not appear to be dose related. In past studies, a dose of 150 mg. per day was approximately as effective as a dose of 600 mg. per day. Accordingly, while dosages in the range of from about 150 mg. per day to about 600 mg. per day are effective, the lower doses are preferred. Because the litholytic effect of the UDCA is enhanced when administered concurrently or in combination with the polyol fatty acid polyesters, doses of UDCA below 150 mg. per day are effective, but complete gallstone dissolution could take longer at such lower doses.

INDUSTRIAL APPLICABILITY

The following non-limiting examples further illustrate the compositions and processes of this invention. It will be appreciated that sugars and sugar alcohols, appropriately esterified, are encompassed by the term "sugar" as used herein and such materials can be interchanged in the compositions. All percentages herein are by weight, unless otherwise specified.

EXAMPLE I

Gelatin capsules for use by the patient with gallstones are prepared by conventional methods, as follows:

| Ingredient | Amount per Capsule |
| --- | --- |
| Sucrose fatty acid polyester* | 1500 mg. |
| Retinol | 0.3 RDA |
| Sodium chenodeoxycholate | 125 mg. |
| Stearic acid | 750 mg. |

*Liquid, mixed hexa-, hepta- and octa-sucrose esters, predominately the octa-ester, esterified with mixed soybean oil fatty acids, predominately in the $C_{16}$-$C_{18}$ chain length.

The capsules of the foregoing type are prepared by simply mixing the ingredients and filling the standard gelatin capsules. Two capsules are administered orally six times daily for a month, and then the dosage is gradually increased (by one capsule per day) until diarrhea occurs. The dosage is then reduced by two capsules per day and held constant for the remainder of therapy. This treatment regimen causes gradual dissolution of radiolucent gallstones. Vitamin A levels in the patients are not decreased significantly from the normal. The patients are not troubled by undesired anal leakage with this regimen.

Similar results are obtained when the sucrose polyester in the capsules of Example I is replaced with an equivalent quantity of a fatty acid polyester selected from the group consisting of glucose tetraoleate, glucose tetrastearate, mixed glucose tetraesters of soybean oil fatty acids, mixed mannose tetraesters of tallow fatty acids, mixed galactose tetraesters of olive oil fatty acids, mixed arabinose tetraesters of cottonseed oil fatty acids, xylose tetralinoleate, galactose pentastearate, sorbitol tetraoleate, sucrose tetrastearate, sucrose pentastearate, sucrose hexaoleate, sucrose heptaoleate, and sucrose octaoleate, respectively.

In the composition of Example I the retinol is replaced by an equivalent dosage level of a commercial vitamin A ester concentrate and equivalent results are secured.

In the composition of Example I, the stearic acid anti-anal leakage ingredient is replaced by an equivalent amount of methyl stearate, ethyl stearate, propyl stearate, methyl behenate, ethyl behenate, hydrogenated palm oil, hydrogenated rapeseed oil and mixed hydrogenated tallow triglycerides, respectively, and equivalent anti-anal leakage results are secured.

Preferred compositions of the type of Example I for causing dissolution of gallstones, especially in the human body, preferably comprise from about 0.1 gram to about 5 grams of mixed hexa-, hepta-, and octa-oleate esters of sucrose polyester, an effective amount (as disclosed hereinabove) of the AAL agent and at least about 0.1 RDA of one or more of the fat-soluble vitamins.

EXAMPLE II

Gelatin capsules comprising a unit dosage form of an AAL agent, a liquid polyester and vitamin E are prepared by conventional means, as follows:

| Ingredient | Amount per Capsule |
| --- | --- |
| Sucrose octaoleate | 3500 mg. |
| Vitamin E* | 0.2 RDA |
| Hydrogenated palm oil | 750 mg. |

*Consists of mixed alpha, beta, gamma and delta tocopherols.

The above capsules are administered orally three times daily (three per meal/70 kg. man). This treatment regimen substantially inhibits cholesterol stone formation in the patient and enhances stone dissolution. No vitamin E deficiency in the patient is noted. No anal leakage from use of the capsules is noted.

The capsules of Example II can be additionally supplemented with sufficient β-carotene to provide a 0.25 RDA of vitamin A per capsule.

The hydrogenated palm oil is replaced by an equivalent amount of tristearin and equivalent anti-anal leakage results are secured.

When oleic acid is used to replace the hydrogenated palm oil, no substantial anti-anal leakage effect is noted.

When the foregoing capsules are administered concurrently with 200 mg./day of sodium ursodeoxycholate, gallstone dissolution is greatly enhanced.

The capsules of Example II are suitable for human use and for veterinary use with horses, cattle, dogs, cats and other animals afflicted with radiolucent gallstones.

EXAMPLE III

Gelatin capsules comprising an AAL agent, a liquid polyester, ursodeoxycholic acid, and containing a mixture of the fat-soluble vitamins are as follows:

| Ingredient | Mg. per Capsule |
| --- | --- |
| Sucrose octaoleate | 750 |
| Vitamin A | 0.1 |
| Vitamin D | 0.01 |
| Vitamin E | 0.1 |
| Vitamin K | 0.1 |
| Ethyl stearate | 750 |
| UDCA | 150 |

The vitamin A employed in the capsules of Example III is retinol; the vitamin D is a 1:1 mixture of irradiated ergosterol and irradiated 7-dehydrocholesterol; the vitamin E comprises a commercial mixture of alpha, beta, gamma and delta tocopherols; and the vitamin K comprises the fat-soluble phylloquinone.

Three capsules of the type prepared in Example III are administered orally five times daily (three with each meal) to inhibit the formation of radiolucent gallstones and cause dissolution of existing cholesterol gallstones in a 70 kg. patient. The body levels of fat-soluble vitamins A, D, E and K do not decrease below normal. No anal leakage is noted. Similar capsules in this dosage range without ethyl stearate can cause an undesired laxative effect, i.e., leakage of polyester through the anal sphincter, in some patients.

EXAMPLE IV

A highly palatable, low calorie composition suitable for use as a cooking fat substitute by individuals on a prophylactic or therapeutic diet is as follows:

| Ingredient | % by Weight |
| --- | --- |
| Cocoa butter | 50 |
| Vitaminized liquid sucrose polyester* | 50 |

*Avg. 7.5 ester of sucrose and unsaturated, mixed soybean oil fatty acids fortified to provide 1000 I.U. of vitamin A per one ounce of composition.

The composition of the foregoing type is used in standard fashion as a cooking fat. The continued use of the composition as a replacement for regular cooking fats lowers the level of cholesterol in the bile but does not cause depletion of vitamin A in the tissues. No anal leakage of the liquid polyester is noted.

In the composition of Example IV the natural cocoa butter is replaced by an equivalent amount of a position-specific triglyceride, and equivalent results are secured.

When the composition of Example IV is administered concurrently with chenodeoxycholic acid therapy, cholesterol gallstone dissolution is greatly enhanced.

EXAMPLE V

A liquid concentrate is prepared according to the following formula:

| Ingredient | % by Weight |
| --- | --- |
| Water | 10 |
| Polyglycerol ester emulsifier T-24 | 5 |
| Propylene glycol monoester | 5 |
| Vitaminized xylitol pentaoleate* | 45 |
| Chenodeoxycholic acid | 2 |
| Light Karo ® syrup | 33 |

*Vitaminized with sufficient irradiated ergosterol to provide 40.0 I.U. of vitamin D per two ounce serving.

The composition of Example V is prepared by thoroughly mixing the indicated ingredients. The composition is consumed alone, in a dose of two tablespoons 3 times daily, or used in making a "milkshake" of ⅔ cup ice cream, ⅔ cup milk, 2 tablespoons of vanilla, chocolate or strawberry syrup, and 2 tablespoons of liquid concentrate per serving, which is consumed in a dose of three servings per day. Continued ingestion of the liquid concentrate of Example V, or foods made therefrom, dissolves existing gallstones and does not result in vitamin D deficiency. No anal leakage of the xylitol pentaoleate is noted.

The composition of Example V is added to commercial, dry animal feed compositions (15% level) to effect gallstone dissolution in sheep and cattle.

EXAMPLE VI

A mayonnaise is prepared according to the following formula:

| Ingredient | % by Weight |
| --- | --- |
| Sucrose - Mixed soybean oil octaester | 62.789 |
| White vinegar (25 grain) | 9.624 |
| Fresh egg yolk | 7.304 |
| Water | 7.512 |
| CDCA | 6.132 |
| Sugar | 1.951 |
| Egg white solids | 1.463 |
| Salt | 1.268 |
| Dry mustard powder | 0.976 |
| Lemon juice | 0.976 |
| Red and Cayenne pepper | 0.005 |
| Total | 100.000 |

When ingested with food in amounts of up to two tablespoons per day, this mayonnaise composition provides suitable dosages of sucrose polyester and chenodeoxycholic acid for dissolution of radiolucent gallstones.

What is claimed is:

1. A composition for prevention and treatment of radiolucent gallstones, comprising:
   (a) a safe and effective amount of a non-absorbable, non-digestible polyol fatty acid polyester wherein the polyol is esterified with at least four fatty acid groups; and
   (b) a safe and effective amount of a litholytic bile acid.

2. A composition according to claim 1 wherein the litholytic bile acid is selected from the group consisting of chenodeoxycholic acid, ursodeoxycholic acid, and their pharmaceutically-acceptable salts, and mixtures thereof.

3. A composition for prevention and treatment of radiolucent gallstones, comprising:
   (a) a non-absorbable, non-digestible liquid polyol fatty acid polyester wherein the polyol is esterified with at least four fatty acid groups;
   (b) a safe and effective amount of a litholytic bile acid; and (c) sufficient anti-anal leakage agent to prevent leakage of said liquid polyester through the anal sphincter.

4. A composition according to claim 3 wherein the litholytic bile acid is selected from the group consisting of chenodeoxycholic acid, ursodeoxycholic acid, and their pharmaceutically-acceptable salts, and mixtures thereof.

5. A composition according to claim 4 wherein the sucrose fatty acid polyester is a member selected from the group consisting of the hexaoleate, haptaoleate and octaoleate of sucrose, and mixtures thereof.

6. A composition according to claim 5 which comprises at least about 10% by weight of the anti-anal leakage agent.

7. A composition for prevention and treatment of radiolucent gallstones, comprising:
 (a) a non-absorbable, non-digestible liquid polyol fatty acid polyester wherein the polyol is esterified with at least four fatty acid groups;
 (b) a safe and effective amount of a litholytic biel acid; and
 (c) sufficient fat-soluble vitamins selected from the group consisting of vitamin A, vitamin D, vitamin E and vitamin K, and mixtures thereof, to prevent abnormally low levels of said fat-soluble vitamins in humans or animals ingesting said composition.

8. A composition according to claim 7 wherein the litholytic bile acid is selected from the group consisting of chenodeoxycholic acid, ursodeoxycholic acid, and their pharmaceutically-acceptable salts, and mixtures thereof.

9. A composition according to claim 8 wherein the polyol fatty acid polyester is selected from the group consisting of sugars and sugar alcohols containing from 4 to 8 hydroxyl groups esterified with fatty acid groups, wherein each fatty acid group has from about 8 to about 22 carbon atoms.

10. A composition according to claim 9 wherein the polyol fatty acid polyester is sucrose fatty acid polyester.

11. A composition according to claim 10 wherein the sucrose fatty acid polyester is selected from the group consisting of the hexaoleate, haptaoleate, and octaoleate of sucrose, and mixtures thereof.

12. A composition according to claim 11 which additionally contains at least about 10% by weight of an anti-anal leakage agent.

13. A method for prevention and treatment of radiolucent gallstones, comprising administering to a human or lower animal in need of such treatment a therapeutically-effective amount of a composition comprising a non-absorbable, non-digestible polyol fatty acid polyester having at least four fatty acid ester groups.

14. A method according to claim 13 wherein the composition administered further comprises a safe and effective amount of a litholytic bile acid.

15. A method according to claim 13 which further comprises the concurrent administration of a composition comprising a safe and effective amount of a litholytic bile acid.

16. A method according to claim 14 or 15 wherein the litholytic bile acid is selected from the group consisting of chenodeoxycholic acid, ursodeoxychloic acid, and their pharmaceutically-acceptable salts, and mixtures thereof.

17. A method according to claim 13, 14, or 15 wherein the polyol fatty acid polyester is selected from the group consisting of sugars and sugar alcohols containing from 4 to 8 hydroxyl groups esterified with fatty acid groups, wherein each fatty acid group has from about 8 to about 22 carbon atoms.

18. A method according to claim 17 wherein the amount of polyester administered is from about 50 milligrams to about 2 grams polyester per kilogram of body weight per day.

19. A method according to claim 18 wherein the sucrose fatty acid polyester is selected from the group consisting of the hexaoleate, heptaoleate and octaoleate of sucrose, and mixtures thereof.

* * * * *